(12) United States Patent
Erickson et al.

(10) Patent No.: US 8,679,408 B2
(45) Date of Patent: Mar. 25, 2014

(54) TOTAL ORGANIC CARBON ANALYSIS

(75) Inventors: Gary L. Erickson, College Station, TX (US); Karl M. Williams, Bryan, TX (US)

(73) Assignee: O.I. Corporation, College Station, TX (US)

( * ) Notice: Subject to any disclaimer, the term of this patent is extended or adjusted under 35 U.S.C. 154(b) by 475 days.

(21) Appl. No.: 12/762,218

(22) Filed: Apr. 16, 2010

(65) Prior Publication Data

US 2010/0267160 A1   Oct. 21, 2010

Related U.S. Application Data

(63) Continuation of application No. 11/350,420, filed on Feb. 9, 2006, now abandoned.

(51) Int. Cl.
| | | |
|---|---|---|
| *G01N 27/00* | (2006.01) | |
| *G01N 15/06* | (2006.01) | |
| *G01N 31/12* | (2006.01) | |
| *G01N 7/00* | (2006.01) | |

(52) U.S. Cl.
USPC ........... 422/83; 422/68.1; 422/80; 422/82.03; 204/416; 204/433

(58) Field of Classification Search
USPC ...................... 422/68.1, 80, 83; 204/416, 433
See application file for complete search history.

(56) References Cited

U.S. PATENT DOCUMENTS

| | | |
|---|---|---|
| 4,336,127 A | 6/1982 | Bertelsen |
| 4,505,801 A | 3/1985 | Detwiler et al. |
| 4,755,473 A | 7/1988 | Nishino et al. |
| 4,977,785 A | 12/1990 | Willoughby et al. |
| 5,209,916 A | 5/1993 | Gruen |
| 5,328,676 A | 7/1994 | Gruen |
| 5,370,855 A | 12/1994 | Gruen |
| 5,462,776 A | 10/1995 | Gruen |
| 5,571,577 A | 11/1996 | Zhang et al. |
| 5,620,512 A | 4/1997 | Gruen |

(Continued)

FOREIGN PATENT DOCUMENTS

| | | |
|---|---|---|
| JP | 60-220854 A | 11/1985 |
| JP | 01-197631 A | 8/1989 |

(Continued)

OTHER PUBLICATIONS

"Shimadzu TOC 5000," Webpage: http: www.gmi-inc.com/AnyLab/Shimadzu%20TOC%205000.htm, pp. 1-3.

(Continued)

*Primary Examiner* — Dean Kwak
(74) *Attorney, Agent, or Firm* — J. Rogers Williams, Jr.; Andrews Kurth LLP

(57) ABSTRACT

The present invention provides an apparatus and method for measuring carbon (any one or all of TC, TOC, or TIC) in a sample matrix. In an embodiment, a method for measuring carbon in a sample composition is provided. The method comprises providing an apparatus comprising a reaction chamber and a diamond coated electrode, wherein the diamond coated electrode is doped with boron. The apparatus further comprises a detector. In addition, the method comprises contacting the sample composition with the electrode. The method further comprises applying an alternating current to the electrode at a sufficient voltage to produce carbon dioxide. Moreover, the method comprises measuring the amount of carbon dioxide produced.

10 Claims, 7 Drawing Sheets

(56) References Cited

U.S. PATENT DOCUMENTS

| | | | |
|---|---|---|---|
| 5,645,645 | A | 7/1997 | Zhang et al. |
| 5,772,760 | A | 6/1998 | Gruen et al. |
| 5,808,178 | A | 9/1998 | Rounbehler et al. |
| 5,849,079 | A | 12/1998 | Gruen et al. |
| 5,855,760 | A | 1/1999 | Zen et al. |
| 5,897,924 | A | 4/1999 | Ulczynski et al. |
| 5,900,127 | A | 5/1999 | Iida et al. |
| 5,902,640 | A | 5/1999 | Krauss et al. |
| 5,902,751 | A * | 5/1999 | Godec et al. .............. 436/146 |
| 5,932,791 | A | 8/1999 | Habitzer et al. |
| 5,970,804 | A | 10/1999 | Robbat, Jr. |
| 5,989,511 | A | 11/1999 | Gruen et al. |
| 6,106,692 | A | 8/2000 | Kunimatsu et al. |
| 6,267,866 | B1 * | 7/2001 | Glesener et al. ............ 205/450 |
| 6,272,905 | B1 | 8/2001 | Drzewiecki |
| 6,305,212 | B1 | 10/2001 | Drzewiecki |
| 6,541,272 | B1 | 4/2003 | Mitra |
| 6,588,266 | B2 | 7/2003 | Tubel et al. |
| 7,314,540 | B2 | 1/2008 | Seki et al. |
| 7,632,393 | B2 | 12/2009 | Kounaves |
| 2003/0170906 | A1 | 9/2003 | Swain et al. |
| 2005/0226774 | A1 | 10/2005 | Kounaves |
| 2007/0183929 | A1 | 8/2007 | Erickson |

FOREIGN PATENT DOCUMENTS

| | | | |
|---|---|---|---|
| WO | 2003/104765 | A3 | 12/2003 |
| WO | WO 03104765 | A2 * | 12/2003 |
| WO | 2007/092665 | A2 | 8/2007 |

OTHER PUBLICATIONS 03734494.2 Supplemental European Search Report, EPO, Jul. 24, 2007.
Hagans P L; Natishan P M; Stoner B R; O'Grady W E: "Electrochemical oxidation of phenol using borondoped diamond electrodes", Journal of the Electrochemical Society, vol. 148, No. 7, Jul. 2001, pp. E298-E301, XP7909722, ISSN: 0013-4651.
Hattori S; Doi M; Takahashi E; Kurosu T; Nara M; Nakamatsu S; Nishiki Y; Furuta T; Iida M: "Electrolytic decomposition of amaranth dyestuff using diamond electrodes", Journal of Applied Electrochemistry, vol. 33, No. 1, Jan. 2003, pp. 85-91, XP2377272, ISSN: 0021-891X.
PCT/US2003/18164 International Search Report, US, Jun. 8, 2004.
Qian et al. "Automated High-Performance, High-temperature Combustion Total Organic Carbon Analyzer," Anal. Chem. 1996, 68, 3090-3097.
Hutte, R. S., Godec, R.D., O'Neill , K.J., Sievers Instrukments Inc., "An Improved Oxidation Reactor for Total Organic Carbon Measurements," SAE Technical Paper Series, vol. 941393, Jun. 20-23, 1994.
Japan Industrial Standards, Organic Carbon (TOC) Automatic Measuring Instrument, Continuous Total Organic Carbon Analyzer K 0805-1988.
PCT International Search Report and Written Opinion for International Application No. PCT/US07/60791 dated Oct. 1, 2007.
PCT International Preliminary Report on Patentability for Application No. PCT/US07/60791 dated Aug. 12, 2008.
PCT International Preliminary Examination Report for Application No. PCT/US03/18164 dated Aug. 6, 2004.
May 27, 2010 Office Action in CA. Serial No. 2,642,150.
Dec. 17, 2008 Office Action in U.S. Appl. No. 11/350,420.
Feb. 10, 2009 Office Action in U.S. Appl. No. 11/350,420.
Dec. 24, 2009 Office Action in U.S. Appl. No. 11/350,420.
Aug. 3, 2009 Notice of Allowance/Allowability in U.S. Appl. No. 10/517,584 (Kounaves).
May 15, 2009 Office Action in U.S. Appl. No. 10/517,584 (Kounaves).
Oct. 29, 2008 Office Action in U.S. Appl. No. 10/517,584 (Kounaves).
Jun. 9, 2009 Final Rejection in JP 2004-511789 (Kounaves) (JP and Eng Tr).
Jan. 6, 2009 First Rejection in JP 2004-511789 (Kounaves) (JP and Eng Tr).
Jan. 29, 2010 Second Examination Report Action in EP 03 734494.2 (Kounaves) (EP).
Sep. 11, 2009 First Examination Report in EP 03 734494.2 (Kounaves) (EP).
Jan. 16, 2009 Response to Dec. 17, 2008 Office Action in U.S. Appl. No. 11/350,420.
Jun. 10, 2009 Response to Feb. 10, 2009 Office Action in U.S. Appl. No. 11/350,420.
Jan. 27, 2009 Response to Oct. 29, 2008 Office Action in U.S. Appl. No. 10/517,584 (Kounaves).
Mar. 31, 2009 Response to Jan. 6, 2009 First Rejection in JP 2004-511789 (Kounaves) (JP and Eng Tr).
Jan. 19, 2010 Response to Sep. 11, 2009 First Examination Report in EP 03 734494.2 (Kounaves) (EP).
Jul. 30, 2010 Response to Jan. 29, 2010 Second Examination Report Action in EP 03 734494.2 (Kounaves) (EP).
Aug. 10, 2010 Third Examination Report Action in EP 03 734494.2 (Kounaves) (EP).
Dec. 20, 2010 Response to Aug. 10, 2010 Third Examination Report in EP 03 734494.2 (Kounaves) (EP).
Jan. 13, 2011 Fourth Examination Report Action in EP 03 734494.2 (Kounaves) (EP).
Mar. 29, 2011 Fifth Examination Report Action in EP 03 734494.2 (Kounaves) (EP).
Jun. 1, 2011 Response to Mar. 29, 2011 Fifth Examination Report in EP 03 734494.2 (Kounaves) (EP).
Jun. 10, 2011 Sixth Examination Report Action in EP 03 734494.2 (Kounaves) (EP).
Ponnuswamy, Thomas, Chen, Jin-Jian, Chyan, Fei Xu and Oliver, Monitoring metal ion contamination onset in hydrofluoric acid using silicon—diamond and dual silicon sensing electrode assembly, The Royal Society of Chemistry 2001, Analyst, 2001, 126, pp. 877-880, www.rsc.org/analyst.

* cited by examiner

TOTAL ORGANIC CARBON ANALYSIS

CROSS-REFERENCE TO RELATED APPLICATIONS

This application is a continuation of U.S. application Ser. No. 11/350,420 filed Feb. 9, 2006, which is incorporated by reference herein in its entirety for all purposes.

BACKGROUND

1. Field of the Invention

This invention relates generally to the field of measuring carbon in a sample composition. More particularly, this invention relates to measuring carbon as Total Organic Carbon (TOC), Total Inorganic Carbon (TIC) or Total Carbon (TC) using electrochemical oxidation.

2. Background of the Invention

The need to measure carbon in aqueous samples exists in matrixes from ultra-pure water to waste water and industrial solutions for a variety of reasons. Historically, the analysis equipment to accurately measure carbon in an aqueous solution involved large equipment and hazardous reagents, such as strong acid and oxidizing agents. The use of electrochemical oxidation of carbon may eliminate at least one of these reagents and, when combined with a detection technique to quantify the resultant carbon dioxide gas (e.g., in solution, measured in a headspace or purged from the sample and transported with carrier gas to a detector), promises a versatile, easy to use, and cost-effective alternative for accurately determining TOC levels in a solution. Thus, the development of a safe and cost-effective electrochemical device capable of oxidizing organic carbon and allowing determination of TOC in a sample composition would represent a significant advance in the art.

Electrodes are used in the typical electrochemical cell for oxidation of carbon. The most common working electrode material has typically been carbon-based or made from metals such as platinum, silver, gold, mercury, or nickel. Drawbacks to such electrodes include poor oxidation. Further drawbacks include the self-consuming nature (e.g., reduction/oxidation) of the electrodes themselves. To overcome these limitations, conductive diamond film electrodes have been developed. Diamond film electrodes include a substrate material coated with diamond or diamond-like film wherein the diamond coated electrodes are doped to provide conductivity (e.g., boron doped). Drawbacks to the conventional diamond or diamond-like film electrodes include the tendency of electrodes to fail due to contamination and corrosion. Additional drawbacks include insufficient oxidation, Consequently, there still remains a need for a method and apparatus for measuring carbon using electrochemical oxidation with reduced electrode contamination and corrosion.

BRIEF SUMMARY

These and other needs in the art are addressed in one embodiment by an apparatus for measuring the carbon concentration of a sample. The apparatus comprises a reaction chamber and a detection system, whereby varying control algorithms allows for the determination of carbon as Total Organic Carbon (TOC), Total Inorganic Carbon (TIC) or Total Carbon (TC). In addition, the apparatus comprises a set of diamond coated electrodes, wherein the diamond coated electrodes may be doped to provide conductivity (e.g., doped with boron).

In another embodiment, these and other needs in the art are addressed by a method for measuring carbon in a sample composition. The method comprises providing an apparatus comprising a reaction chamber with a set of diamond coated electrodes, wherein the diamond coated electrodes may be doped with boron. The apparatus further comprises a detection system to determine $CO_2$ concentrations in the gas phase, liquid phase or a combination of the two. In addition, the method comprises contacting the sample composition with the electrode. The method further comprises applying a sufficiently controlled voltage to the electrode to produce carbon dioxide. Moreover, the method comprises measuring the amount of carbon dioxide produced.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

The following description details a method and an apparatus for measuring carbon in an aqueous sample composition. Without being limited by theory, the method and apparatus are capable of measuring carbon with minimum contamination to the electrodes resulting in longer effective use and superior cost efficiency. Two electrodes provide the oxidation capability. The control system for these electrodes may optimize the self-cleaning nature of the electrodes. The apparatus may be configured to process discrete samples or for continuous sampling using appropriate electrode geometries. The geometries include but are not limited to batch or flow through designs. The geometries may include fixed or variable gap electrodes of any design that allows the electrodes electrical isolation.

Figure 1:
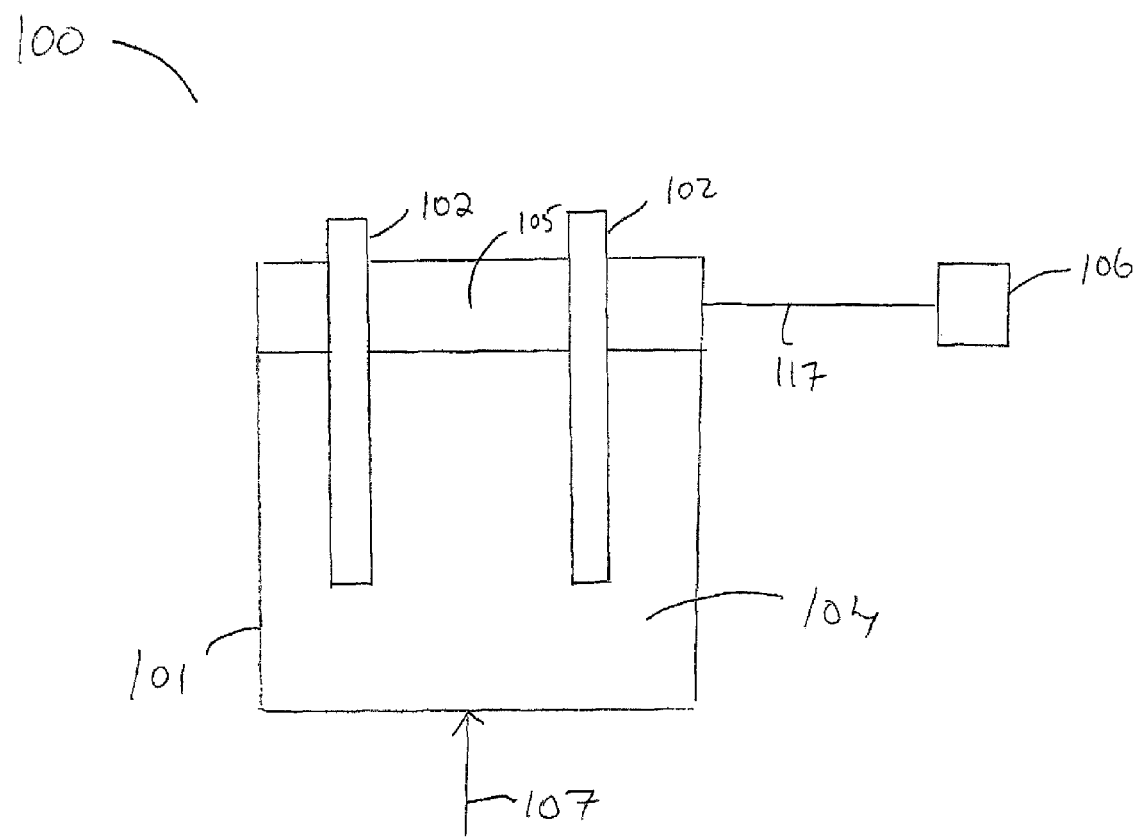
FIG. 1 illustrates an embodiment of a carbon analyzer comprising a remote detector.
Figure 2:
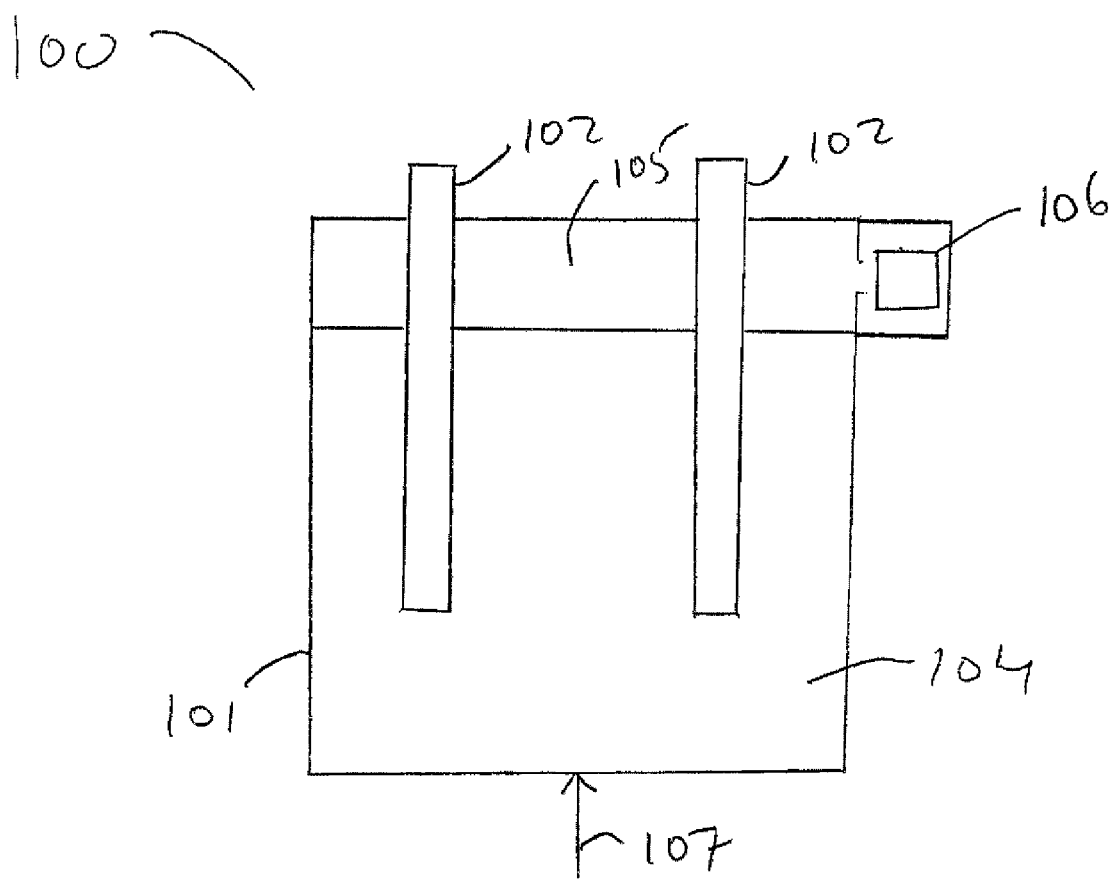
FIG. 2 illustrates an embodiment of a carbon analyzer comprising a detector.

FIG. 1 illustrates a carbon analyzer 100 comprising a reaction chamber 101, electrodes 102, and a detector 106. Reaction chamber 101 comprises any configuration and material sufficient to create a sealed system whereby carbon dioxide may not escape prior to its detection. In the embodiment illustrated in FIG. 1, carbon analyzer 100 comprises two electrodes 102. It is to be understood that carbon analyzer 100 is not limited to two electrodes 102, but in an alternative embodiment (not illustrated) carbon analyzer 100 comprises three electrodes. In such an alternative embodiment, carbon analyzer 100 comprises two electrodes 102 and may also include a third electrode that may be used as a reference electrode. For instance, the two electrodes 102 may be arranged in such a fashion that they are comprised of multiple pieces and may be electrically activated in pairs or in some other manner. The third electrode may physically be a part of a new circuit and may not contribute to the oxidation per se, but instead provides a monitoring function. The monitoring function may include providing feedback as to the operation of the primary electrodes or the oxidation process, or as a reference electrode for an independent (from TOC, TIC, TC) analytical technique (such as scanning Voltametry). Detector 106 comprises any detector suitable for detecting the presence of carbon dioxide. As illustrated, detector 106 is a gas phase detector. Gas phase detectors refer to detectors that can measure the concentration of carbon dioxide in a gas. Without limitation, examples of suitable gas phase detectors include nondispersed infrared detectors, laser diode detectors, electrochemical cells, Fourier Transform Infrared (FTIR) detectors, and the like. In an alternative embodiment (not illustrated), carbon analyzer 100 comprises more than one detector 106 in which at least one detector 106 is a gas phase detector, and at least one detector 106 is a liquid phase detector. Liquid phase detectors refer to detectors that can measure the concentration of carbon dioxide in a liquid. Without limitation, examples of suitable liquid phase detectors include fluorescence detectors, ion selective electrodes, ion selective probes, conductivity cells, and the like. As shown in FIG. 1, detector 106 is remote from reaction chamber 101 with gas from reaction chamber 101 fed to detector 106 by line 117. In an alternative embodiment as shown in FIG. 2, detector 106 may be directly connected to reaction chamber 101.

Figure 3:
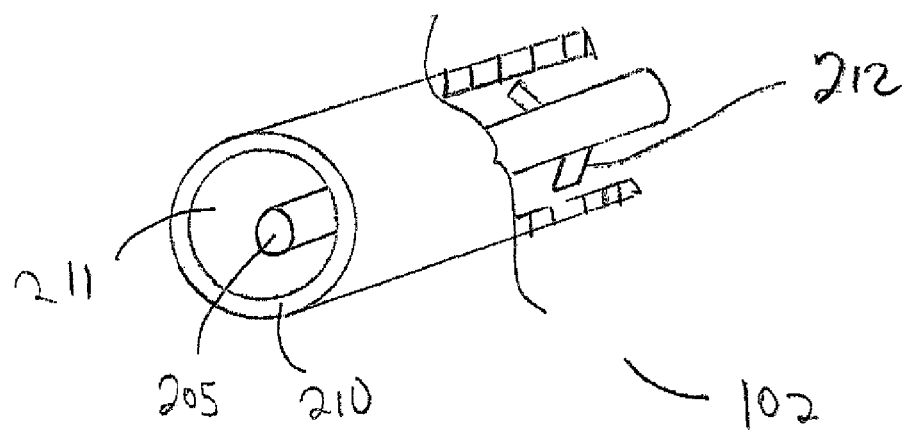
FIG. 3 illustrates a side view of an electrode configuration.

In an embodiment as shown in FIG. 3, reactor geometry is illustrated for flow through operation where electrode 102 comprises an inner element 205 and an outer element 210 that are concentric to each other with a fixed gap flow path 211 for the oxidation. Inner element 205 and outer element 210 each comprise a substrate that is coated with diamond. The substrate may be comprised of any suitable material including but not limited to nickel, platinum, palladium, silicon, niobium, titanium, or combinations thereof. The diamond coating may be applied by any suitable method such as by chemical vapor deposition. Diamond coating includes coatings of diamond and/or diamond-like materials. Without limitation, diamond-like materials include hard, amorphous films with a significant fraction of $sp^3$-hybridized carbon atoms and which may contain a significant amount of hydrogen. Depending on the deposition conditions, these films may be fully amorphous or contain diamond crystallites.

Figure 4:
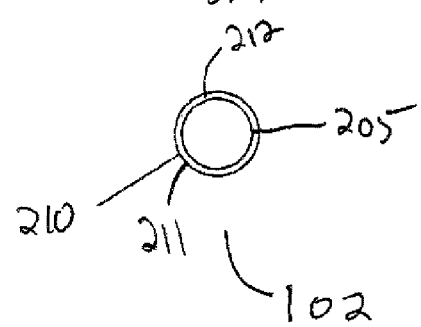
FIG. 4 illustrates an end view of an electrode configuration.

In an embodiment, the diamond coated substrates of inner and outer elements 205, 210 are doped with a doping material. Without limitation, examples of suitable doping materials include boron, zinc, nitrogen, phosphorous, and sulfur. In an embodiment, the doping material is boron. The diamond coated substrates may be doped by any suitable method such as during chemical vapor deposition. FIG. 4 illustrates an end view of electrode 102 showing concentric inner and outer elements 205, 210.

As further illustrated in FIG. 3, inner and outer elements 205, 210 may comprise any suitable shapes for oxidizing carbon to carbon dioxide. In an embodiment, inner element 205 may have a substantially solid, partially hollow, or substantially hollow interior. Outer element 210 comprises a hollow interior of a suitable diameter for inner element 205 to be disposed therein. In an embodiment, inner element 205 comprises a solid shape such as a rod and outer element 210 comprises a hollow interior suitable for containing inner element 205. In a preferred embodiment, inner element 205 comprises a rod, and outer element 210 comprises a hollow tube. In other preferred embodiments, inner and outer elements 205, 210 comprise mesh such as mesh tubes. In such other preferred embodiments, electrode 102 comprises concentric mesh tubes (e.g., inner and outer elements 205, 210). In another preferred embodiment, inner element 205 comprises a rod, and outer element 210 comprises a mesh tube.

It is to be further understood that the configuration of electrode 102 is not limited to the configuration illustrated in FIG. 3 but instead can include any suitable configuration for use in carbon analyzer 100. For instance, other suitable geometries of electrode 102 include parallel plates, tortuous path, or any other geometry that allows for fixed or variable gap electrodes of any design that allows the electrodes electrical isolation.

As shown in FIGS. 3 and 4, some embodiments include electrode 102 comprising an insulator 212 that is disposed between inner element 205 and outer element 210 in a geometry that allows sample flow. The sample flows through fixed gap flow path 211 and is in contact with both inner element 205 and outer element 210. Insulator 212 may comprise any suitable, non-combustible material. Without limitation, examples of suitable materials include ceramic, glass, or combinations thereof. It is to be understood that electrodes 102 are not limited to the configuration embodiments as discussed above but may also comprise any suitable configuration for electrochemical oxidation. In any such suitable configurations, electrodes 102 comprise the substrate coated with diamond and optionally doped with a doping material (e.g., boron).

As shown in FIG. 1, a sample composition 104 is placed in reaction chamber 101. Sample composition 104 may comprise any aqueous solution containing carbon.

As further shown in FIG. 1, electrodes 102 are contacted with sample composition 104. For instance, electrodes 102 are at least partially immersed in sample composition 104. Controlled voltage is applied to electrodes 102 for a sufficient time to generate oxidation radicals in sample composition 104. Without being limited by theory, the current generated by the application of the voltage may cause an oxidation reaction to occur in sample composition 104. As a result, carbon dioxide may be formed in the presence of any carbon based compounds. The voltage may be applied for any period of time suitable for producing carbon dioxide. Without being limited by theory, the desired time may depend on the composition of sample composition 104, the geometry of reaction chamber 101, and/or the type of electrode 102 used. In some embodiments, the voltage may be applied for a time period between about 0.5 minutes and about 30 minutes, alternatively about 2 minutes. In an embodiment, the voltage may be applied to electrodes 102 in an alternating current (AC) format. The AC voltage may be supplied by any suitable power source capable of producing AC voltage. The AC voltage may be applied at a frequency between about 1 Hz and about 100 Hz, alternatively between about 100 Hz and about 1 kHz, and alternatively between about 1 kHz and about 1 MHz, further alternatively between about 1 kHz and about 200 MHz, and further alternatively between about 1 kHz and about 1 GHz. In an embodiment, the frequency is about 10 Hz. In an embodiment, any suitable frequency may be chosen to optimize the current density and maintain clean electrodes. In further embodiments, the AC voltage may be applied in a sinusoidal wave form. Any suitable AC voltage may be applied to the electrodes. In an embodiment, AC voltage may be applied at greater than ½ cell plus potential voltage drop across the sample due to conductivity. In another embodiment, AC voltage may be applied at a voltage greater than 2.5 V, alternatively from about 5 V to about 300 V, and alternatively from about 5 V to about 200 V, and further alternatively from about 5 V to about 150 V. In some embodiments, the AC voltage may be applied at a voltage from about 5 V to about 12 V. Without being limited by theory, the specific control algorithm for the application of a voltage may prevent oxidation and contamination of the electrodes. Further, without being limited by theory, such voltage ranges allow oxidation without the use of reagents.

As shown in FIG. 1, a carrier gas 107 is introduced to reaction chamber 101. In an embodiment, a suitable amount of carrier gas 107 is introduced to facilitate transport of carbon dioxide from sample composition 104 to headspace 105. Carrier gas 107 may be supplied during or after the voltage is applied to electrodes 102. Carrier gas 107 may comprise any inert gas suitable for transporting carbon dioxide. Without limitation, examples of suitable carrier gases include nitrogen, helium, argon, or combinations thereof. In an alternative embodiment (not illustrated), no carrier gas 107 is introduced to reaction chamber 101. Carbon dioxide flows from head space 105 to detector 106 via line 117. Detector 106 measures the amount of carbon dioxide produced. By measuring the amount of carbon dioxide produced, the amount of organics within sample composition 104 may be determined. Without being limited by theory, the amount of carbon dioxide measured may be directly proportional to the amount of organics that may be present in sample composition 104. Using samples containing known quantities of dissolved organics, a standard curve may be generated to allow for the determination of a precise concentration of organics within the test solution. In an alternative embodiment (not illustrated), at least one liquid phase detector 106 may be used to measure the amount of carbon dioxide present in sample composition 104.

Figure 5:
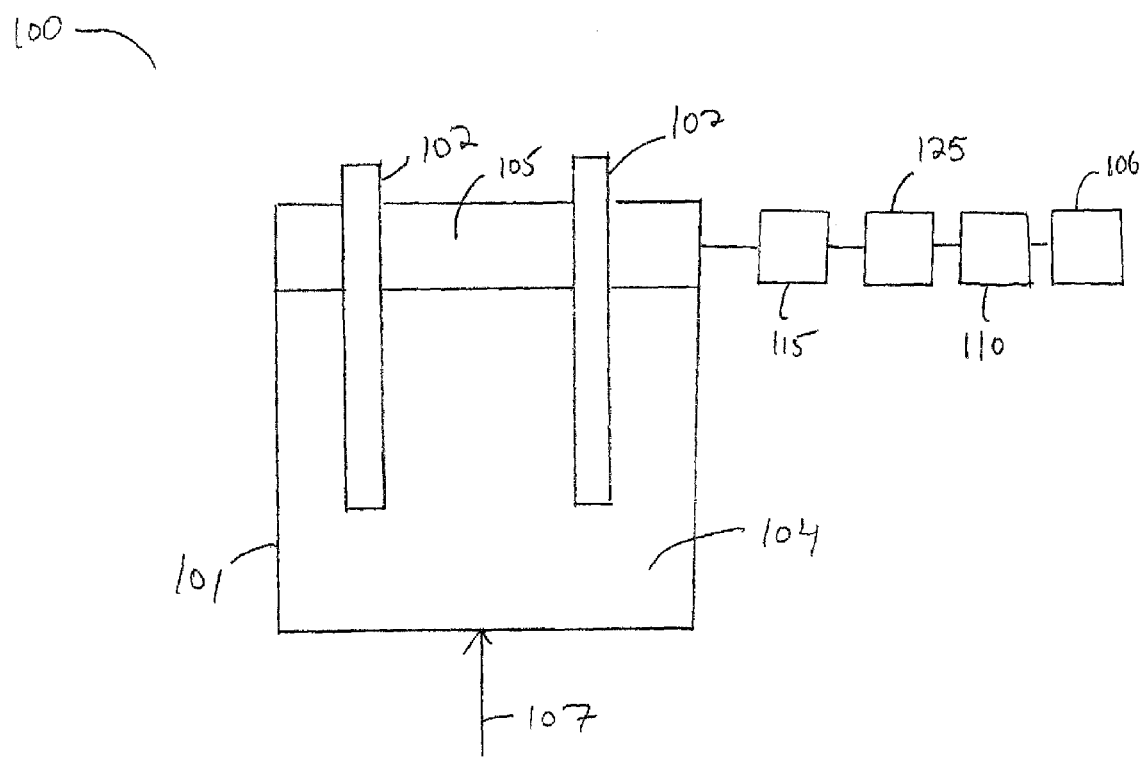
FIG. 5 illustrates an embodiment of a carbon analyzer comprising a drier, a scrubber, and a trap.

In an alternative embodiment, the carbon dioxide may be dried in a drier to remove moisture prior to being measured by detector 106. Without limitation, examples of suitable driers include a dryer permeation tube or an anhydrous tube. In another alternative embodiment, the carbon dioxide may be passed through a scrubber to remove acid vapors from the carbon dioxide. In further embodiments, the carbon dioxide may be directed into a trap, from which it is released into detector 106. Any suitable trap may be used that may retain carbon dioxide until a suitable amount of carbon dioxide is accumulated prior to release to detector 106. FIG. 5 illustrates an embodiment in which carbon analyzer 100 comprises a reaction chamber 101, electrodes 102, detector 106, drier 115, scrubber 125, and a trap 110.

Figure 6:
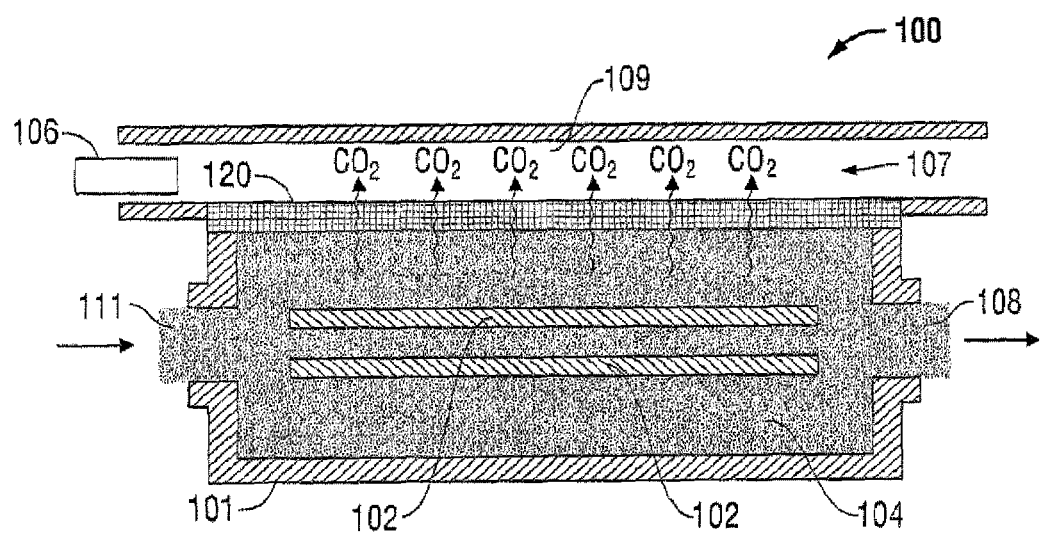
FIG. 6 illustrates an embodiment of a carbon analyzer comprising a gas diffusion membrane.

FIG. 6 illustrates an embodiment in which carbon analyzer 100 comprises a reaction chamber 101, electrodes 102, detector 106, and a collection chamber 109. The sample composition 104 may be directed through the inlet 111 and into reaction chamber 101 wherein sample composition 104 is contacted with electrodes 102. While sample composition 104 passes through reaction chamber 101, voltage may be applied to electrodes 102 to oxidize carbon based compounds in sample composition 104. Sample composition 104 may exit via outlet 108 of reaction chamber 101.

Figure 7:
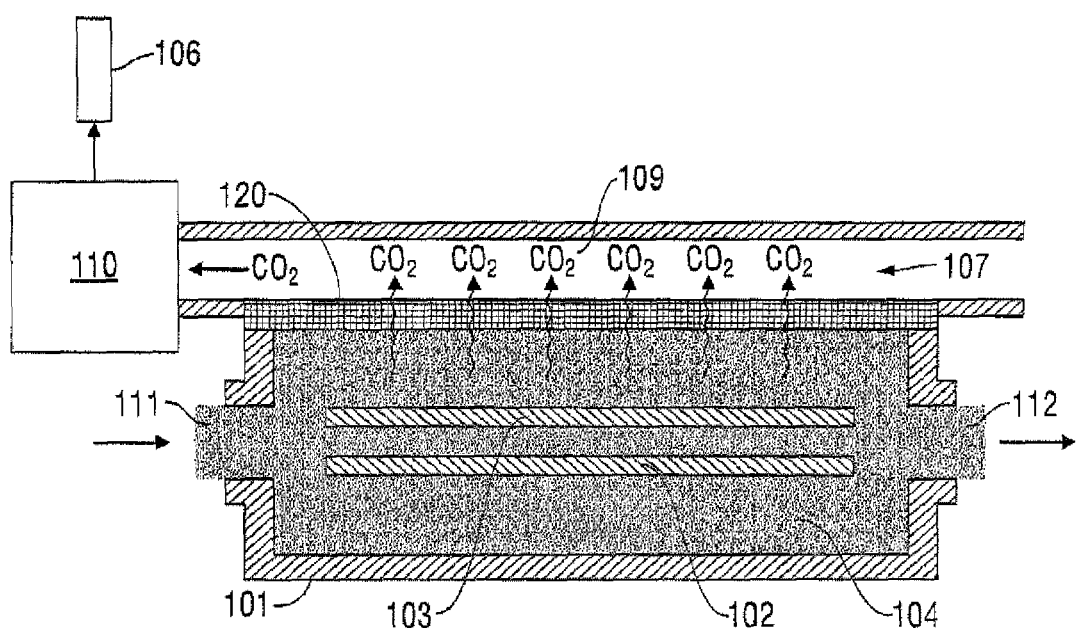
FIG. 7 illustrates an embodiment of a carbon analyzer comprising a gas diffusion membrane and a trap.

As further shown in FIG. 6, the carbon dioxide that may be formed may diffuse out of sample composition 104 through a gas diffusion membrane 120 and into collection chamber 109. Gas diffusion membrane 120 may comprise any material suitable for diffusion therethrough of carbon dioxide but that substantially prevents diffusion of liquid. Without limitation, examples of suitable membrane materials include polypropylene, cellophanes, or combinations thereof. For instance, a commercial example of a membrane material is TEFLON, which is available from E. I. DuPont de Nemoirs and Company. The carbon dioxide may pass through gas diffusion membrane 120 into collection chamber 109. In an embodiment, collection chamber 109 is on the opposite side of gas diffusion membrane 120 from sample composition 104. Collection chamber 109 may comprise the form of a tube or any other suitable shape for collecting carbon dioxide and allowing the carbon dioxide to be fed to detector 106 for measurement. Carrier gas 107 may be fed to collection chamber 109 to transport the carbon dioxide to detector 106. In an embodiment as shown in FIG. 7, carrier gas 107 directs the carbon dioxide to trap 110, from which the carbon dioxide is released to detector 106 for measurement. In further embodiments (not illustrated), the carbon dioxide may be additionally passed through a drier and/or a scrubber after passing through membrane 120.

Figure 8:
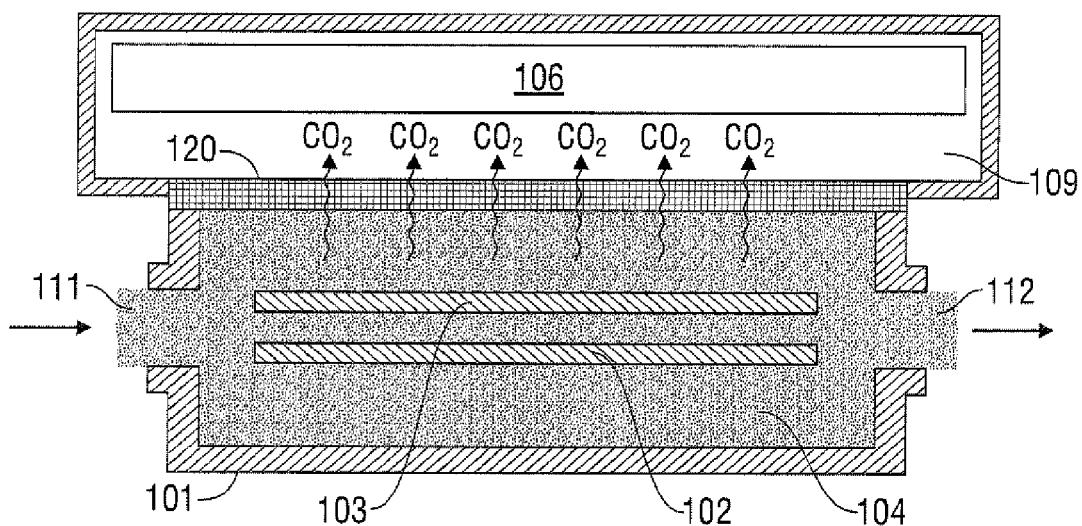
FIG. 8 illustrates an embodiment of a carbon analyzer comprising a gas diffusion membrane and a detector disposed within a collection chamber.

In an embodiment as illustrated in FIG. 8, detector 106 is disposed within collection chamber 109. The carbon dioxide may diffuse through membrane 120 and be directly measured by detector 106.

Although the present invention and its advantages have been described in detail, it should be understood that various changes, substitutions and alterations may be made herein without departing from the spirit and scope of the invention as defined by the appended claims.

We claim:

1. An apparatus for measuring carbon in a sample composition, comprising:
    a reaction chamber comprising a gas space and a sample space, wherein the sample space is configured to contain a sample composition comprising an aqueous solution comprising carbon;
    two, and no more than two, electrodes configured to contact with the sample composition, wherein the two electrodes comprise a first electrode, wherein the first electrode comprises a substrate coated with a diamond-like material that is doped with a doping material, wherein each of the two electrodes is adapted and configured to electrochemically oxidize carbon in the sample composition to carbon dioxide, wherein the two electrodes are electrically activated as a pair, wherein the two electrodes are electrically isolated, and wherein either one of the two electrodes is a working electrode; and
    a means for detecting gas-phase carbon dioxide in the gas space, wherein the means for detecting gas-phase carbon dioxide in the gas space is directly connected to the reaction chamber,
    and a sealed system, wherein the sealed system comprises the means for detecting gas-phase carbon dioxide, the reaction chamber and the two electrodes.

2. The apparatus of claim 1, further comprising a liquid phase carbon dioxide detector.

3. The apparatus of claim 1, wherein the diamond-like material comprises diamonds.

4. The apparatus of claim 1, wherein the diamond-like material comprises a hard amorphous film with a significant fraction of $sp^3$-hybridized carbon atoms.

5. The apparatus of claim 1, wherein the doping material comprises at least one of boron, zinc, nitrogen, phosphorus and sulfur.

6. The apparatus of claim 1, wherein the first electrode is connected to an alternating-current voltage source.

7. The apparatus of claim 1, further comprising a collection chamber and a gas diffusion membrane interposed between the sample composition and the collection chamber.

8. The apparatus of claim 7, wherein the means for detecting gas-phase carbon-dioxide in the gas space is configured to detect carbon dioxide in the collection chamber.

9. The apparatus of claim 1, wherein the sealed system does not include a dryer.

10. The apparatus of claim 1, wherein the substrate comprises nickel, platinum, palladium, silicon, niobium, titanium, or combination thereof.

\* \* \* \* \*